United States Patent
Tsubata et al.

(10) Patent No.: US 11,197,806 B2
(45) Date of Patent: Dec. 14, 2021

(54) SOLID COSMETIC COMPOSITION COMPRISING A FATTY ACID-BASED GELLING AGENT AND A CO-GELLING AGENT

(71) Applicant: L'OREAL, Paris (FR)

(72) Inventors: Kazuyoshi Tsubata, Tokyo (JP); Chisato Masumoto, Kawasaki (JP)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/344,307

(22) PCT Filed: Oct. 17, 2017

(86) PCT No.: PCT/JP2017/038097
§ 371 (c)(1),
(2) Date: Apr. 23, 2019

(87) PCT Pub. No.: WO2018/084005
PCT Pub. Date: May 11, 2018

(65) Prior Publication Data
US 2019/0269581 A1    Sep. 5, 2019

(30) Foreign Application Priority Data

Nov. 1, 2016  (JP) .............................. JP2016-214234

(51) Int. Cl.
| *A61K 8/04* | (2006.01) |
| *A61K 8/25* | (2006.01) |
| *A61K 8/31* | (2006.01) |
| *A61K 8/34* | (2006.01) |
| *A61K 8/36* | (2006.01) |
| *A61K 8/73* | (2006.01) |
| *A61K 8/89* | (2006.01) |
| *A61K 8/92* | (2006.01) |
| *A61Q 1/00* | (2006.01) |
| *A61Q 17/04* | (2006.01) |
| *A61Q 1/12* | (2006.01) |
| *A61Q 1/02* | (2006.01) |
| *A61K 8/58* | (2006.01) |
| *A61K 8/365* | (2006.01) |

(52) U.S. Cl.
CPC ................ *A61K 8/042* (2013.01); *A61K 8/25* (2013.01); *A61K 8/31* (2013.01); *A61K 8/342* (2013.01); *A61K 8/361* (2013.01); *A61K 8/365* (2013.01); *A61K 8/585* (2013.01); *A61K 8/73* (2013.01); *A61K 8/732* (2013.01); *A61K 8/89* (2013.01); *A61K 8/922* (2013.01); *A61K 8/925* (2013.01); *A61Q 1/00* (2013.01); *A61Q 1/02* (2013.01); *A61Q 1/12* (2013.01); *A61Q 17/04* (2013.01); *A61K 2800/31* (2013.01)

(58) Field of Classification Search
CPC ...................................................... A61K 8/042
See application file for complete search history.

(56) References Cited

U.S. PATENT DOCUMENTS

| 5,744,130 A | 4/1998 | Guskey et al. |
| 6,171,601 B1 | 1/2001 | Gardlik et al. |
| 2001/0018045 A1 | 8/2001 | Chuah et al. |
| 2002/0051757 A1 | 5/2002 | Clare et al. |
| 2004/0229984 A1 | 11/2004 | Yamato et al. |

FOREIGN PATENT DOCUMENTS

| CN | 1400891 A |   | 3/2003 |
| EP | 1287816 A1 |   | 3/2003 |
| EP | 1623696 A1 |   | 2/2006 |
| EP | 2329808 A1 |   | 6/2011 |
| JP | 04-091010 A |   | 3/1992 |
| JP | 04-091011 A |   | 3/1992 |
| JP | H09-13074 A |   | 1/1997 |
| JP | 2000-143454 A |   | 5/2000 |
| JP | 2001-039817 A |   | 2/2001 |
| JP | 2001039817 A | * | 2/2001 |
| JP | 2002003340 A | * | 1/2002 |
| JP | 2002-302412 A |   | 10/2002 |
| JP | 2002-316971 A |   | 10/2002 |
| JP | 2002-338425 A |   | 11/2002 |

OTHER PUBLICATIONS

PCT International Search Report dated Jan. 4, 2018 from corresponding PCT Application No. PCT/JP2017/038097 (4 pages).
KIPO, Office Action for the corresponding Korean patent application No. 10-2019-7011696, dated Aug. 10, 2020, with English translation.
JPO, Office Action for the corresponding Japanese patent application No. 2016-214234, dated Jul. 6, 2020, with English translation.
CNIPA, Office Action for the corresponding Chinese patent application No. 201780065627.7, dated Jun. 29, 2021, with English translation.

* cited by examiner

*Primary Examiner* — Gina C Justice
(74) *Attorney, Agent, or Firm* — Lucas & Mercanti, LLP

(57) ABSTRACT

A solid state, oil gel composition for keratinous substance, such as skin, contains (a) at least one fatty acid-based gelling agent; (b) at least one polysaccharide fatty acid ester; and (c) at least one oil. An embodiment according to the present invention provides improved storage stability, morphological stability, and application property.

15 Claims, No Drawings

SOLID COSMETIC COMPOSITION COMPRISING A FATTY ACID-BASED GELLING AGENT AND A CO-GELLING AGENT

CROSS-REFERENCE TO RELATED APPLICATIONS

This application is a 371 of PCT/JP2017/038097, filed on Oct. 17, 2017, which claims benefit of Japanese Patent Application No. 2016-214234 filed on Nov. 1, 2016.

TECHNICAL FIELD

The present invention relates to a cosmetic composition, in particular a solid cosmetic composition comprising a fatty acid-based gelling agent and a co-gelling agent, for a keratin substance such as skin.

BACKGROUND ART

Solid state cosmetic compositions for a keratin substance, such as a foundation, are generally applied on a keratin substance, such as skin, with a sponge applicator to make an attractive appearance, to conceal imperfections, such as blemishes, wrinkles, and pores, and to protect the keratin substance from UV rays. These solid state cosmetic compositions include mainly oil and fillers. For such solid state cosmetic compositions, their storage stability, morphological stability, and application property are among key properties. In order to improve these properties, in general, gelling or solidifying agents can be used in the compositions.

Up to now, some prior art documents relating to solid state cosmetic products comprising gelling or solidifying agents have been published.

JP-A-H04-91010 discloses a transparent solid cosmetic composition comprising 12-hydroxystearic acid, a transparent liquid oil component having 120 or less of hydroxyl values, and methylphenylpolysiloxane.

JP-A-H04-91011 discloses a transparent solid cosmetic composition comprising 12-hydroxystearic acid, a transparent liquid oil component having 120 or less of hydroxyl values, and a component selected from oleic acid ester of aliphatic alcohol, fatty acid ester of oleyl alcohol, and triglycerides in which ≥60wt. % of constituent fatty acids are unsaturated fatty acids comprising 18 to 20 of carbon atoms.

JP-A-2000-143454 discloses an oily hair cosmetic composition comprising 12-hydroxystearic acid, one or more hydrocarbon oil, and one or more silicone derivatives.

However, there is still a demand for solid state cosmetic products with improved properties.

DISCLOSURE OF INVENTION

An objective of the present invention is to provide a solid cosmetic composition for a keratin substance, such as skin, which has improved storage stability, morphological stability, and application property.

The above objective of the present invention can be achieved by an oil gel composition comprising:
(a) at least one fatty acid-based gelling agent;
(b) at least one polysaccharide fatty acid ester; and
(c) at least one oil.

The fatty acid-based gelling agent may be selected from saturated linear fatty acids comprising at least one hydroxyl group and 12 to 24 carbon atoms, and esters or amides thereof, and a combination thereof.

Preferably, the fatty acid-based gelling agent is 12-hydroxystearic acid.

The polysaccharide fatty acid ester may be selected from esters of dextrin or inulin with one or more fatty acids selected from myristic acid, oleic acid, palmitic acid, stearic acid, isopalmitic acid, and isostearic acid.

Preferably, the polysaccharide fatty acid ester is dextrin myristate.

The oil may be selected from oils of plant or animal origin, synthetic oils, silicone oils, hydrocarbon oils, fatty alcohols, and mixtures thereof.

An amount of the fatty acid-based gelling agent may range from 0.1 to 20% by weight, preferably from 0.5 to 15% by weight, more preferably from 1 to 10% by weight, and in particular from 2 to 8% by weight relative to the total weight of the composition.

An amount of the polysaccharide fatty acid ester may range from 0.01 to 15% by weight, preferably from 0.05 to 10% by weight, more preferably from 0.1 to 8% by weight, and in particular from 0.2 to 5% by weight relative to the total weight of the composition.

A weight ratio of the (a) fatty acid-based gelling agent to the (b) polysaccharide fatty acid ester may be from 1 to 30, preferably from 2 to 20, and more preferably from 3 to 12.

An amount of the oil may be at least 30% by weight, preferably at least 35% by weight, and more preferably at least 40% by weight, relative to the total weight of the composition.

In one embodiment of the present invention, the composition further comprises at least one inorganic filler selected from talc, mica, synthetic mica, and silica.

The inorganic filler may be hydrophobically surface-treated.

In one embodiment of the present invention, the composition further comprises at least one organic filler.

In another embodiment of the present invention, the composition further comprises at least one organic UV filter.

The present invention also relates to a method for preparing the composition according to the present invention by mixing the fatty acid-based gelling agent, the polysaccharide fatty acid ester, and the oil.

The present invention also relates to a cosmetic process for a keratin substance such as skin, comprising the step of applying onto the keratin substance the composition according to the present invention with an applicator.

BEST MODE FOR CARRYING OUT THE INVENTION

After diligent research, the inventor have found that a combination of a fatty acid-based gelling agent and polysaccharide fatty acid ester can surprisingly improve storage stability, morphological stability, and application property of oil-based cosmetics for skin, and thus completed the present invention.

Thus, the oil gel composition for keratin substance, preferably skin, according to the present invention comprises:
(a) at least one fatty acid-based gelling agent;
(b) at least one polysaccharide fatty acid ester; and
(c) at least one oil.

The composition according to the present invention can provide oil gel cosmetic compositions with improved storage stability, morphological stability, and application property. In addition, the composition according to the present invention is able to provide a keratinous substance with superior cosmetic effects.

Hereafter, the composition according to the present invention will be described in a detailed manner.

[Composition]

The oil gel composition according to the present invention comprises (a) at least one fatty acid-based gelling agent, (b) at least one polysaccharide fatty acid ester, and (c) at least one oil.

The oil gel composition according to the present invention is in a solid state. For the purposes of the invention, the term "solid" characterizes the state of the composition at a temperature of 25° C. In particular, the composition according to the invention has, at a temperature of 25° C. and at atmospheric pressure (760 mmHg), a hardness of greater than 10, preferably greater than 40, and more preferably greater than 50 when measured by Texture Analyzer under the condition below.

Product: TA. XT plus, Stable Microsystems:
Mobile: P/3
Test speed: 1.0 mm/sec
Distance: 2 mm
Trigger force: 2.0 g (Fatty Acid-Based Gelling Agent)

The composition according to the present invention comprises (a) at least one fatty acid-based gelling agent. Two or more (a) fatty acid-based gelling agents may be used in combination. Thus, a single type of a fatty acid-based gelling agent or a combination of different types of fatty acid-based gelling agents may be used.

The (a) fatty acid-based gelling agent used in the present invention includes gelling agents of fatty acids, esters of fatty acids, amides of fatty acids, and a combination thereof. The fatty acid used in the fatty acid-based gelling agents may preferably be saturated linear fatty acids comprising at least one hydroxyl group and 12 to 24 carbon atoms, and in particular 12-hydroxystearic acid. Therefore, the (a) fatty acid-based gelling agents can be 12-hydroxystearic acid, esters of 12-hydroxystearic acids, or amides of 12-hydroxystearic acids, or a combination of thereof.

Preferably, the (a) fatty acid-based gelling agents are selected from 12-hydroxystearic acid, 12-hydroxystearic acid methyl ester, 12-hydroxystearic acid ethyl ester, 12-hydroxystearic acid stearyl ester, 12-hydroxystearic acid benzyl ester, 12-hydroxystearic acid amide, isopropyl amide of 12-hydroxystearic acid, butyl amide of 12-hydroxystearic acid, benzyl amide of 12-hydroxystearic acid, phenyl amide of 12-hydroxystearic acid, t-butyl amide of 12-hydroxystearic acid, cyclohexyl amide of 12-hydroxystearic acid, 1-adamantyl amide of 12-hydroxystearic acid, 2-adamantyl amide of 12-hydroxystearic acid, diisopropyl amide of 12-hydroxystearic acid, and combinations thereof.

Most preferably, the (a) fatty acid-based gelling agent is 12-hydroxystearic acid.

The amount of the (a) fatty acid-based gelling agent in the composition according to the present invention may be 0.1% by weight or more, preferably 0.5% by weight or more, more preferably 1% by weight or more, in particular from 2% by weight or more, relative to the total weight of the composition.

The amount of the (a) fatty acid-based gelling agent in the composition according to the present invention may be 20% by weight or less, preferably 15% by weight or less, more preferably 10% by weight or less, in particular 8% by weight or less, relative to the total weight of the composition.

The amount of the (a) fatty acid-based gelling agent in the composition according to the present invention may range from 0.1 to 20% by weight, preferably from 0.5 to 15% by weight, more preferably from 1 to 10% by weight, in particular from 2 to 8% by weight, relative to the total weight of the composition.

(Polysaccharide Fatty Acid Ester)

The composition according to the present invention comprises (b) at least one polysaccharide fatty acid ester. Two or more (b) polysaccharide fatty acid esters may be used in combination. Thus, a single type of polysaccharide fatty acid ester or a combination of different types of polysaccharide fatty acid esters may be used. The (b) polysaccharide fatty acid ester is used as a co-gelling agent with the (a) fatty acid-based gelling agent in the composition.

The polysaccharides in the (b) polysaccharide fatty acid ester include, but are not limited to, dextrin and inulin. The fatty acids in the (b) polysaccharide fatty acid ester include, but are not limited to, linear or branched, saturated or unsaturated $C_{10}$-$C_{24}$, preferably $C_{12}$-$C_{20}$ fatty acids, for example, myristic acid, oleic acid, palmitic acid, stearic acid, isopalmitic acid, and isostearic acid.

Preferably, the (b) polysaccharide fatty acid ester is selected from dextrin palmitate, dextrin myristate, dextrin stearate, dextrin oleate, dextrin isopalmitate, dextrin isostearate, dextrin palmitate/2-ethylhexanoate, dextrin palmitate/stearate, dextrin palmitate/octanoate, and inulin stearate, and mixtures thereof.

The amount of (b) polysaccharide fatty acid ester in the composition according to the present invention may be 0.01% by weight or more, preferably 0.05% by weight or more, more preferably 0.1% by weight or more, and in particular 0.2% by weight or more, relative to the total weight of the composition.

The amount of (b) polysaccharide fatty acid ester in the composition according to the present invention may be 15% by weight or less, preferably 10% by weight or less, more preferably 8% by weight or less, and in particular 5% by weight or less, relative to the total weight of the composition.

The amount of (b) polysaccharide fatty acid ester in the composition according to the present invention may be from 0.01 to 15% by weight, preferably from 0.05 to 10% by weight, more preferably from 0.1 to 8% by weight, and in particular from 0.2 to 5% by weight relative to the total weight of the composition.

In one embodiment of the present invention, the (b) polysaccharide fatty acid ester is included in the composition in a less amount than the amount of the (a) fatty acid-based gelling agent.

In another embodiment of the present invention, the composition comprises the (a) fatty acid-based gelling agent and the (b) polysaccharide fatty acid ester in a weight ratio of the (a) fatty acid-based gelling agent to the (b) polysaccharide fatty acid ester being from 1 to 30:1, preferably from 2 to 20:1, and more preferably from 3 to 12:1.

(Oil)

The composition according to the present invention comprises (c) at least one oil. Two or more (c) oils may be used in combination. Thus, a single type of oil or a combination of different types of oils may be used.

Here, "oil" means a fatty compound or substance which is in the form of a liquid or a paste (non-solid) at room temperature (25° C.) under atmospheric pressure (760 mmHg). As the oils, those generally used in cosmetics can be used alone or in combination thereof. These oils may be volatile or non-volatile.

The (c) oil may be a non-polar oil such as a hydrocarbon oil, a silicone oil, or the like; a polar oil such as a plant or animal oil and an ester oil or an ether oil; or a mixture thereof.

The (c) oil may be selected from oils of plant or animal origin, synthetic oils, silicone oils, hydrocarbon oils and fatty alcohols, and mixtures thereof.

As examples of plant oils, mention may be made of, for example, linseed oil, camellia oil, macadamia nut oil, corn oil, mink oil, olive oil, avocado oil, sasanqua oil, castor oil, safflower oil, jojoba oil, sunflower oil, almond oil, rapeseed oil, sesame oil, soybean oil, peanut oil, and mixtures thereof.

As examples of animal oils, mention may be made of, for example, squalene and squalane.

As examples of synthetic oils, mention may be made of alkane oils such as isododecane and isohexadecane, ester oils, ether oils, and artificial triglycerides.

The ester oils are preferably liquid esters of saturated or unsaturated, linear or branched $C_1$-$C_{26}$ aliphatic monoacids or polyacids and of saturated or unsaturated, linear or branched $C_1$-$C_{26}$ aliphatic monoalcohols or polyalcohols, the total number of carbon atoms of the esters being greater than or equal to 10.

Preferably, for the esters of monoalcohols, at least one from among the alcohol and the acid from which the esters of the present invention are derived is branched.

Among the monoesters of monoacids and of monoalcohols, mention may be made of ethyl palmitate, ethyl hexyl palmitate, isopropyl palmitate, dicaprylyl carbonate, alkyl myristates such as isopropyl myristate or ethyl myristate, isocetyl stearate, 2-ethylhexyl isononanoate, isononyl isononanoate, isodecyl neopentanoate, and isostearyl neopentanoate.

Esters of $C_4$-$C_{22}$ dicarboxylic or tricarboxylic acids and of $C_1$-$C_{22}$ alcohols, and esters of monocarboxylic, dicarboxylic, or tricarboxylic acids and of non-sugar $C_4$-$C_{26}$ dihydroxy, trihydroxy, tetrahydroxy, or pentahydroxy alcohols may also be used.

Mention may especially be made of: diethyl sebacate; isopropyl lauroyl sarcosinate; diisopropyl sebacate; bis(2-ethylhexyl) sebacate; diisopropyl adipate; di-n-propyl adipate; dioctyl adipate; bis(2-ethylhexyl) adipate; diisostearyl adipate; bis(2-ethylhexyl) maleate; triisopropyl citrate; triisocetyl citrate; triisostearyl citrate; glyceryl trilactate; glyceryl trioctanoate; trioctyldodecyl citrate; trioleyl citrate; neopentyl glycol diheptanoate; diethylene glycol diisononanoate.

As ester oils, one can use sugar esters and diesters of $C_6$-$C_{30}$ and preferably $C_{12}$-$C_{22}$ fatty acids. It is recalled that the term "sugar" means oxygen-bearing hydrocarbon-based compounds containing several alcohol functions, with or without aldehyde or ketone functions, and which comprise at least 4 carbon atoms. These sugars may be monosaccharides, oligosaccharides, or polysaccharides.

Examples of suitable sugars that may be mentioned include sucrose (or saccharose), glucose, galactose, ribose, fucose, maltose, fructose, mannose, arabinose, xylose, and lactose, and derivatives thereof, especially alkyl derivatives, such as methyl derivatives, for instance methylglucose.

The sugar esters of fatty acids may be chosen especially from the group comprising the esters or mixtures of esters of sugars described previously and of linear or branched, saturated or unsaturated $C_6$-$C_{30}$ and preferably $C_{12}$-$C_{22}$ fatty acids. If they are unsaturated, these compounds may have one to three conjugated or non-conjugated carbon-carbon double bonds.

The esters according to this variant may also be selected from monoesters, diesters, triesters, tetraesters, and polyesters, and mixtures thereof.

These esters may be, for example, oleates, laurates, palmitates, myristates, behenates, cocoates, stearates, linoleates, linolenates, caprates, and arachidonates, or mixtures thereof such as, especially, oleopalmitate, oleostearate, and palmitostearate mixed esters, as well as pentaerythrityl tetraethyl hexanoate.

More particularly, use is made of monoesters and diesters and especially sucrose, glucose, or methylglucose monooleates or dioleates, stearates, behenates, oleopalmitates, linoleates, linolenates, and oleostearates.

An example that may be mentioned is the product sold under the name Glucate® DO by the company Amerchol, which is a methylglucose dioleate.

As examples of preferable ester oils, mention may be made of, for example, diisopropyl adipate, dioctyl adipate, 2-ethylhexyl hexanoate, ethyl laurate, cetyl octanoate, octyldodecyl octanoate, isodecyl neopentanoate, myristyl propionate, 2-ethylhexyl 2-ethylhexanoate, 2-ethylhexyl octanoate, 2-ethylhexyl caprylate/caprate, methyl palmitate, ethyl palmitate, isopropyl palmitate, dicaprylyl carbonate, isopropyl lauroyl sarcosinate, isononyl isononanoate, ethylhexyl palmitate, isohexyl laurate, hexyl laurate, isocetyl stearate, isopropyl isostearate, isopropyl myristate, isodecyl oleate, glyceryl tri(2-ethylhexanoate), pentaerythrithyl tetra(2-ethylhexanoate), 2-ethylhexyl succinate, diethyl sebacate, and mixtures thereof.

As examples of artificial triglycerides, mention may be made of, for example, capryl caprylyl glycerides, glyceryl trimyristate, glyceryl tripalmitate, glyceryl trilinolenate, glyceryl trilaurate, glyceryl tricaprate, glyceryl tricaprylate, glyceryl tri(caprate/caprylate), and glyceryl tri(caprate/caprylate/linolenate).

As examples of silicone oils, mention may be made of, for example, linear organopolysiloxanes such as dimethylpolysiloxane, methylphenylpolysiloxane, methylhydrogenpolysiloxane, and the like; cyclic organopolysiloxanes such as cyclohexasiloxane, octamethylcyclotetrasiloxane, decamethylcyclopentasiloxane, dodecamethylcyclohexasiloxane, and the like; and mixtures thereof.

Preferably, the silicone oil is chosen from liquid polydialkylsiloxanes, especially liquid polydimethylsiloxanes (PDMS) and liquid polyorganosiloxanes comprising at least one aryl group.

These silicone oils may also be organomodified. The organomodified silicones that can be used in accordance with the present invention are silicone oils as defined above and comprise in their structure one or more organofunctional groups attached via a hydrocarbon-based group.

Organopolysiloxanes are defined in greater detail in Walter Noll's *Chemistry and Technology of Silicones* (1968), Academic Press. They may be volatile or non-volatile.

If they are volatile, the silicones are more particularly chosen from those having a boiling point of between 60° C. and 260° C.

Non-volatile polydialkylsiloxanes may also be used. These non-volatile silicones are more particularly chosen from polydialkylsiloxanes, among which mention may be made mainly of polydimethylsiloxanes containing trimethylsilyl end groups.

Among these polydialkylsiloxanes, mention may be made, in a non-limiting manner, of the following commercial products:

the Silbione® oils of the 47 and 70 047 series or the Mirasil® oils sold by Rhodia, for instance the oil 70 047 V 500 000;

the oils of the Mirasil® series sold by the company Rhodia;

the oils of the 200 series from the company Dow Corning, such as DC200 with a viscosity of 60 000 mm$^2$/s; and the Viscasil® oils from General Electric and certain oils of the SF series (SF 96, SF 18) from General Electric.

Mention may also be made of polydimethylsiloxanes containing dimethylsilanol end groups known under the name dimethiconol (CTFA), such as the oils of the 48 series from the company Rhodia.

Among the silicones containing aryl groups, mention may be made of polydiarylsiloxanes, especially polydiphenylsiloxanes and polyalkylarylsiloxanes such as phenyl silicone oil.

Examples that may be mentioned include products sold under the following names:

the Silbione® oils of the 70 641 series from Rhodia;

the oils of the Rhodorsil® 70 633 and 763 series from Rhodia;

the oil Dow Corning 556 Cosmetic Grade Fluid from Dow Corning;

the silicones of the PK series from Bayer, such as the product PK20;

certain oils of the SF series from General Electric, such as SF 1023, SF 1154, SF 1250, and SF 1265.

As the phenyl silicone oil, phenyl trimethicone is preferable.

The organomodified liquid silicones may especially contain polyethyleneoxy and/or polypropyleneoxy groups. Mention may thus be made of the silicone KF-6017 proposed by Shin-Etsu, and the oils Silwet® L722 and L77 from the company Union Carbide.

Hydrocarbon oils may be chosen from:

linear or branched, optionally cyclic, $C_6$-C16 lower alkanes. Examples that may be mentioned include hexane, undecane, dodecane, tridecane, and isoparaffins, for instance isohexadecane, isododecane, and isodecane; and linear or branched hydrocarbons containing more than 16 carbon atoms, such as liquid paraffins, liquid petroleum jelly, polydecenes and hydrogenated polyisobutenes such as Parleam®, and squalane.

As preferable examples of hydrocarbon oils, mention may be made of, for example, linear or branched hydrocarbons such as isohexadecane, isododecane, squalane, mineral oil (e.g., liquid paraffin), paraffin, vaseline or petrolatum, naphthalenes, and the like; hydrogenated polyisobutene, isoeicosan, and decene/butene copolymer; and mixtures thereof.

The term "fatty" in the fatty alcohol means the inclusion of a relatively large number of carbon atoms. Thus, alcohols which have 4 or more, preferably 6 or more, and more preferably 12 or more carbon atoms are encompassed within the scope of fatty alcohols. The fatty alcohol may be saturated or unsaturated. The fatty alcohol may be linear or branched.

The fatty alcohol may have the structure R—OH wherein R is chosen from saturated and unsaturated, linear and branched radicals containing from 4 to 40 carbon atoms, preferably from 6 to 30 carbon atoms, and more preferably from 12 to 20 carbon atoms. In at least one embodiment, R may be chosen from $C_{12}$-$C_{20}$ alkyl and $C_{12}$-$C_{20}$ alkenyl groups. R may or may not be substituted with at least one hydroxyl group.

As examples of the fatty alcohol, mention may be made of lauryl alcohol, cetyl alcohol, stearyl alcohol, isostearyl alcohol, behenyl alcohol, undecylenyl alcohol, myristyl alcohol, octyldodecanol, hexyldecanol, oleyl alcohol, linoleyl alcohol, palmitoleyl alcohol, arachidonyl alcohol, erucyl alcohol, and mixtures thereof.

It is preferable that the fatty alcohol be a saturated fatty alcohol.

Thus, the fatty alcohol may be selected from straight or branched, saturated or unsaturated $C_6$-$C_{30}$ alcohols, preferably straight or branched, saturated $C_6$-$C_{30}$ alcohols, and more preferably straight or branched, saturated $C_{12}$-$C_{20}$ alcohols.

The term "saturated fatty alcohol" here means an alcohol having a long aliphatic saturated carbon chain. It is preferable that the saturated fatty alcohol be selected from any linear or branched, saturated $C_6$-$C_{30}$ fatty alcohols. Among the linear or branched, saturated $C_6$-$C_{30}$ fatty alcohols, linear or branched, saturated $C_{12}$-$C_{20}$ fatty alcohols may preferably be used. Any linear or branched, saturated $C_{16}$-$C_{20}$ fatty alcohols may be more preferably used. Branched $C_{16}$-$C_{20}$ fatty alcohols may be even more preferably used.

As examples of saturated fatty alcohols, mention may be made of lauryl alcohol, cetyl alcohol, stearyl alcohol, isostearyl alcohol, behenyl alcohol, undecylenyl alcohol, myristyl alcohol, octyldodecanol, hexyldecanol, and mixtures thereof. In one embodiment, cetyl alcohol, stearyl alcohol, octyldodecanol, hexyldecanol, or a mixture thereof (e.g., cetearyl alcohol) as well as behenyl alcohol, can be used as a saturated fatty alcohol.

According to at least one embodiment, the fatty alcohol used in the composition according to the present invention is preferably chosen from cetyl alcohol, octyldodecanol, hexyldecanol, and mixtures thereof.

It is preferable that the oil be chosen from hydrocarbon oils, ester oils, silicone oils, and mixtures thereof.

In one embodiment, it is preferable that the oil be selected from mineral oil, octyldodecanol, petrolatum, isododecane, phenyl silicone oil, hydrogenated polyisobutene, isopropyl myristate, isononyl isononanoate, dimethicone, cyclohexasiloxane, $C_{20-22}$ alcohol, cetyl palmitate, oleyl alcohol, cetyl alcohol and mixtures thereof.

The (c) oil can form an oil phase of the composition according to the present invention.

The (c) oil phase may include the organic UV filter.

The amount of the (c) oil in the composition according to the present invention may be at least 30% by weight, preferably at least 35% by weight, and more preferably at least 40% by weight, relative to the total weight of the composition. The upper limit of the amount of (c) oil in the composition according present invention is not limited to, but in general 99% by weight, preferably 90% by weight, more preferably 80% by weight, and in particular 70% by weight, relative to the total weight of the composition.

(Other Ingredients)

Filler(s)

The composition according to the present invention may preferably include one or more organic and/or inorganic fillers.

The term "fillers" should be understood to mean colorless or white, mineral or synthetic particles of any shape, which are insoluble in the medium of the composition, irrespective of the temperature at which the composition is manufactured.

The fillers may be of any shape, platelet-shaped, spherical or oblong, irrespective of the crystallographic form (for example lamellar, cubic, hexagonal, orthorhombic, etc.).

As the inorganic fillers, mention may be made of talc, mica, silica, magnesium aluminium silicate, trimethyl siloxysilicate, kaolin, bentone, calcium carbonate, magnesium hydrogen carbonate, hydroxyapatite, boron nitride, fluorphlogopite, sericite, calcinated talc, calcinated mica, calcinated sericite, synthetic mica, lauroyl lysine, metal soap, bismuth oxychloride, barium sulfate, magnesium carbonate, and mixtures thereof, optionally hydrophilic- or hydrophobic-treated. Preferably, the inorganic fillers have been hydrophobically surface-treated with, for example, silicone.

As the organic fillers, mention may be made of (meth) acrylic or (meth)acrylate powders, for example, polymethylmethacrylate powders; polyacrylonitrile powders; organopolysiloxane powders, polyamide powders, poly-β-alanine powders and polyethylene powders, polytetrafluoroethylene powders, lauroyllysine, starch, tetrafluoroethylene polymer powders, hollow polymer microspheres, for example comprising an (alkyl)acrylate, metal soaps derived from organic carboxylic acids containing from 8 to 22 carbon atoms, for example zinc stearate, magnesium stearate, lithium stearate, zinc laurate, magnesium myristate, silicone resin microbeads, polyurethane powders, carnauba microwaxes, synthetic microwaxes, microwaxes formed from a mixture of carnauba wax and polyethylene wax, microwaxes formed from a mixture of carnauba wax and of synthetic wax, and polyethylene microwaxes.

The filler may be present in a content ranging from 1% to 50% by weight, preferably from 5% to 45% by weight and more preferably from 10% to 40% by weight relative to the total weight of the composition.

Organic UV Filter(s)

The composition according to the present invention may preferably include one or more organic UV filters which are also called as "lipophilic UV filters"

The organic UV filter used in the present invention may be selected from solid organic UV filters. Preferably, the organic UV filters of the present invention consist of only solid UV organic filters and do not include liquid organic UV filers. The term "liquid" means liquid at 25° C. and at atmospheric pressure (760 mmHg).

The organic UV filter used in the present invention may include, but are not limited to, triazine compounds, para-aminobenzoic acid compounds, salicylic compounds, cinnamate compounds, such as ethylhexyl methoxycinnamate, β,β-diphenylacrylate compounds, such as octocrylene, benzylidenecamphor compounds, phenylbenzimidazole compounds, imidazoline compounds, benzalmalonate compounds, and mecocyanine compounds, and a combination thereof.

The organic UV filter may be present in a content ranging from 0.1% to 20% by weight, preferably from 1% to 15% by weight, and more preferably from 5% to 10% by weight relative to the total weight of the composition.

Colouring Agent(s)

The compositions according to the invention may preferably comprise one or more colouring agent, which may be chosen from pigments, water-soluble or liposoluble dyes, nacres, and glitter flakes, that are well known to those skilled in the art, and mixtures thereof. Especially, the composition includes pigments as the colouring agent.

The term "pigments" should be understood as meaning white or coloured, mineral or organic particles that are insoluble in an aqueous solution. As the pigments that may be used in the invention, mention may be made of titanium oxide, zirconium oxide or cerium oxide, and also zinc oxide, iron oxide or chromium oxide, ferric blue, manganese violet, ultramarine blue and chromium hydrate.

The colouring agent may be present in a content ranging from 0.1% to 10% by weight, preferably from 0.5% to 7% by weight and more preferably from 1% to 5% by weight relative to the total weight of the composition.

Additive(s)

The composition according to the present invention may comprise additives as long as they do not impair the effects of the present invention and they are acceptable in cosmetic use. The additives may be selected from anionic, cationic, nonionic or amphoteric polymers; natural or synthetic thickeners; another gelling agent; natural extracts derived from animals or vegetables; waxes; cosmetically acceptable hydrophobic organic solvents; peptides and derivatives thereof; protein hydrolyzates; preservatives; bactericides; inorganic UV filters; vitamins or provitamins; fragrances; stabilizers, and mixtures thereof.

The amount of the additives is not limited, but may be from 0.1 to 30% by weight relative to the total weight of the composition according to the present invention.

The composition of the present invention may be a cosmetic composition for a keratin substance, preferably a skin cosmetic make-up composition. The composition according to the present invention can be provided in the form of a compact powder, in particular powdery foundations.

The composition according to the present invention is preferably anhydrous or contains less than 3% by weight of water and preferably less than 1% by weight of water, relative to the total weight of the composition. The term "anhydrous" especially means that water is preferably not deliberately added to the composition, but may be present in trace amount in the various compounds used in the composition.

The composition according to the present invention can be manufactured by mixing the (a) at least one fatty acid-based gelling agent, (b) at least one polysaccharide fatty acid ester, and (c) at least one oil to prepare a homogenous oil mixture. In the case that at least one of the above ingredients is solid at room temperature, the ingredients can be heated until it is dissolved. Optionally, if powder ingredients, such as fillers and pigments, are used, they are added to the oil mixture and mixed to be homogenous. In this case, it is preferred that the powder ingredients to be added have been mixed beforehand.

[Cosmetic Process]

The composition according to the present invention may preferably be used as a cosmetic composition for a keratinous substance such as skin. In particular, the composition according to the present invention may be intended for application onto a keratin substance such as the skin, the scalp and/or the lips, preferably the skin. The composition is generally applied on a keratin substance, such as skin, with a sponge applicator to make an attractive appearance, to conceal imperfections, such as blemishes, wrinkles, and pores, and to protect the keratin substance from UV rays.

Therefore, the present invention also relates to a cosmetic process including the step of applying to skin, preferably the face, the composition according to the present invention. The cosmetic process preferably includes making up and/or caring for the skin, preferably facial skin. The composition can be picked up with an applicator, such as a sponge, puff, or brush, by rubbing off the powder. Then the composition is moved from the applicator to the skin by contacting the applicator on the skin.

The composition used according to the present invention is preferably intended to be used as a leave-in type cosmetic composition. The term "leave-in" means a composition that is not intended to be washed out or removed immediately after application.

The inventor surprisingly found that the combination of the fatty acid-based gelling agent and polysaccharide fatty acid ester can improve storage stability, morphological stability, and application property of oil gel cosmetics for skin. Therefore, the invention also relates to a use of the combination of the fatty acid-based gelling agent and polysaccharide fatty acid ester as gelling agents for an oil-based cosmetic composition.

EXAMPLES

The present invention will be described in a more detailed manner by way of examples. However, these examples should not be construed as limiting the scope of the present invention.

[Composition]

The compositions according to Examples 1 to 3 and Comparative Examples 1 to 4, compositions of which are shown in Table 1, were prepared in accordance with a following preparation protocol. In Table 1, all components are based on "parts by weight" as active raw materials. 12-hidroxystearic acid was obtained from THAI KAWAKEN CO., LTD, and dextrin palmitate (trade name: RHEOPEARL KL2) was obtained from CHIBA FLOUR MILLING.

3) Adding the powder mixture into the oil mixture and manually blend with a spatula.

4) Mixing the mixture obtained in step (3) with a speed mixer at 3,000 rpm for 4 minutes.

5) Reheating the mixture obtained in step (4) and pouring a part of it into a metal pan and then pressing it with an electrical pressing machine to obtain a test sample of a solid composition according to each of Examples 1 to 3 and Comparative Examples 1 to 4.

[Evaluation]

(Storage Stability)

The prepared test composition according to each of Examples 1 to 3 and Comparative Examples 1 to 4 was stored in an oven with controlled temperature following 12 hour cycle as shown below for one month. Then, the composition was evaluated on its aspects, odor, and hardness. The storage stability was assessed with the following criteria.

<Cycle (1 cycle=12 hours)>
cooling the sample from 40° C. to −5° C. for 3 hours
keeping the sample at −5° C. for 3 hours
heating the sample from −5° C. to 40° C. for 3 hours
keeping the sample at 40° C. for 3 hours <Criteria>
Good: the composition maintained its initial aspects, odor, and hardness at right after its preparation
Poor: one or more of the aspects, odor, and hardness was deteriorated (Morphological Stability)

TABLE 1

| | Ex. 1 | Ex. 2 | Ex. | Comp. Ex. 1 | Comp. Ex. 2 | Comp. Ex. 3 | Comp. Ex. 4 |
|---|---|---|---|---|---|---|---|
| Sericite surface-treated with silicone | 26.1 | 26.1 | 19.95 | 26.1 | 26.1 | 26.1 | 26.1 |
| Polymethylmethacrylate powder | — | — | 6.1 | — | — | — | — |
| Silica surface-treated with silicone | 5.4 | 5.4 | 5.4 | 5.4 | 5.4 | 5.4 | 5.4 |
| $TiO_2$ surface-treated with silicone | 7.8 | 7.8 | 7.8 | 7.8 | 7.8 | 7.8 | 7.8 |
| Iron oxide | 1.7 | 1.7 | 1.7 | 1.7 | 1.7 | 1.7 | 1.7 |
| Hydrogenated polyisobutene | 44.7 | — | 44.7 | 45.2 | — | 44.7 | 44.7 |
| Phenyl silicone | — | 44.7 | — | — | 45.2 | — | — |
| 12-Hydroxystearic acid | 4 | 4 | 4.25 | 4 | 4 | 4 | 4 |
| Dextrin palmitate | 0.5 | 0.5 | 0.3 | — | — | — | — |
| Polyethylene | — | — | — | — | — | 0.5 | — |
| Hydrogenated caster oil | — | — | — | — | — | — | 0.5 |
| Ethylhexyl methoxycinnamate | 6.8 | 6.8 | 6.8 | 6.8 | 6.8 | 6.8 | 6.8 |
| Octocrylene | 3 | 3 | 3 | 3 | 3 | 3 | 3 |
| Total | 100 | 100 | 100 | 100 | 100 | 100 | 100 |

[Preparation Protocol]

1) Weighing and putting sericite surface-treated with silicone, polymethylmethacrylate powder (Example 3), silica surface-treated with silicone, $TiO_2$ surface-treated with silicone, and iron oxide into a mixer (Hanil mixer) to prepare a powde mixture.

2) Weighing and putting hydrogenated polyisobutene or phenyl silicone, 12-hydroxystearic acid, dextrin palmitate (Examples 1 to 3), polyethylene (Comparative Example 3), hydrogenated caster oil (Comparative Example 4), ethylhexyl methoxycinnamate, and octocrylene into a glass bealer, heating around 70 to 80° C. until solid state components are dissolved, and then mixing them to obtain a homogeneous oil mixture.

The prepared test composition according to each of Examples 1 to 3 and Comparative Examples 1 to 4 was picked up with a standard sponge material as an applicator for a powdery foundation composition, in accordance with a powder foundation application routine. Changes in shape of the composition by sharing stress with an applicator during a picking-up gesture were observed, and the morphological stability was assessed with the following criteria.

Good: the composition maintained its shape after sharing stress
Fair: there were some changes in shape due to the sheering stress but the composition still maintained its usability
Poor: the shape of the composition was broken due to the sheering stress (Application Property)

The test composition picked-up with the applicator was applied on facial skin. The application property was assessed with the following criteria.

Good: the composition was easy to spread on the skin and capable to be applied with the similar way to conventional foundation products Poor: It was difficult to be applied on the skin The results of these evaluations are shown in Table 2.

TABLE 2

|  | Ex. 1 | Ex. 2 | Ex. 3 | Comp. Ex. 1 | Comp. Ex. 2 | Comp. Ex. 3 | Comp. Ex. 4 |
| --- | --- | --- | --- | --- | --- | --- | --- |
| Storage Stability | Good | Good | Good | Good | Good | Poor | Good |
| Morphological stability | Good | Good | Good | Poor | Fair | Good | Good |
| Application property | Good | Good | Good | n.d. | Poor | Poor | Poor |

The compositions according to Examples 1 to 3 including a combination of the fatty acid-based gelling agent and the polysaccharide fatty acid ester exhibited good storage stability, good morphological stability and good application property.

On the other hand, the compositions according to Comparative Examples 1 and 2, which do not comprise the fatty acid-based gelling agent and polysaccharide fatty acid ester, exhibited deteriorated morphological stability or application property. Specifically, the composition according to Comparative Example 1, which includes hydrogenated isobutene as an oil, showed poor morphological stability. The composition according to Comparative Example 2, which includes phenyl silicone as an oil, showed usable morphological stability, but did not show practical application property. The composition according to Comparative Example 3, which includes polyethylene as a gelling agent instead of the combination of the gelling agent and the co-gelling agent of the present invention, exhibited poor storage stability and application property. The composition according to Comparative Example 4, which includes hydrogenated castor oil as a gelling agent instead of the combination of the gelling agent and the co-gelling agent of the present invention, exhibited poor application property.

(Sensory Test)

The composition according to Example 3 was evaluated on its performance as a cosmetic for the skin with a sensory panel evaluation and an instrumental wear test in the same manner as those for a conventional powder foundation.

The composition according to Example 3 gave a superior radiant look on the skin and exhibited a preferable matte effect in light of long lastingness and oil control.

These evaluation results indicate that the present invention has a great benefit since it provides an oil gel cosmetic composition having improved storage stability, morphological stability and application property. Furthermore, the composition according to the present invention produces desirable cosmetic effects, for example, a provision of a radiation look and a matte effect to a keratinous substance.

The invention claimed is:

1. An oil gel composition comprising:
    (a) at least one fatty acid-based gelling agent;
    (b) at least one polysaccharide fatty acid ester, wherein the polysaccharide fatty acid ester is selected from esters of dextrin or inulin with one or more fatty acids selected from myristic acid, oleic acid, palmitic acid, stearic acid, isopalmitic acid, and isostearic acid;
    (c) at least one oil; and
    (d) at least one filler in an amount ranging from 10% to 50% by weight relative to the total weight of the composition,
    wherein a weight ratio of the (a) fatty acid-based gelling agent to the (b) polysaccharide fatty acid ester is from 3 to 30, and an amount of the polysaccharide fatty acid ester ranges from 0.01 to 5% by weight relative to the total weight of the composition.

2. The composition according to claim 1, wherein the fatty acid-based gelling agent is selected from saturated linear fatty acids comprising at least one hydroxyl group and 12 to 24 carbon atoms, and esters or amides thereof, and a combination thereof.

3. The composition according to claim 2, wherein the fatty acid-based gelling agent is 12-hydroxystearic acid.

4. The composition according to claim 1, wherein the polysaccharide fatty acid ester is dextrin myristate.

5. The composition according to claim 1, wherein the oil is selected from oils of plant or animal origin, synthetic oils, silicone oils, hydrocarbon oils, fatty alcohols, and mixtures thereof.

6. The composition according to claim 1, wherein an amount of the fatty acid-based gelling agent ranges from 0.1 to 20% by weight relative to the total weight of the composition.

7. The composition according to claim 1, wherein an amount of the polysaccharide fatty acid ester ranges from 0.05 to 5% by weight relative to the total weight of the composition.

8. The composition according to claim 1, wherein a weight ratio of the (a) fatty acid-based gelling agent to the (b) polysaccharide fatty acid ester is from 3 to 20.

9. The composition according to claim 1, wherein an amount of the oil is at least 30% by weight relative to the total weight of the composition.

10. The composition according to claim 1, wherein the at least one filler comprises at least one inorganic filler selected from talc, mica, synthetic mica, and silica which may be hydrophobically surface-treated.

11. The composition according to claim 1, wherein the at least one filler comprises at least one organic filler.

12. The composition according to claim 1, further comprising at least one organic UV filter.

13. The composition according to claim 1, wherein the oil in the composition is consisted of at least one selected from the group consisting of mineral oil, octyldodecanol, petrolatum, isododecane, phenyl silicone oil, isopropyl myristate, isononyl isononanoate, dimethicone, cyclohexasiloxane, $C_{20-22}$ alcohol, cetyl palmitate, oleyl alcohol, cetyl alcohol.

14. A method for preparing the composition according to claim 1, comprising:
    mixing the fatty acid-based gelling agent, the polysaccharide fatty acid ester, the oil, and the filler.

15. A cosmetic process for a keratin substance, comprising:
    applying onto the keratin substance the composition according to claim 1 with an applicator.

* * * * *